(12) United States Patent
Lee et al.

(10) Patent No.: US 7,828,742 B2
(45) Date of Patent: Nov. 9, 2010

(54) METHOD AND SYSTEM OF MONITORING RESPIRATORY SIGNAL BY RADIO

(75) Inventors: In Kwang Lee, Cheongju (KR); Kyung Ah Kim, Cheongju (KR); Eun Jong Cha, Cheongju (KR)

(73) Assignees: Chungbuk National University (KR); Industry Academic Cooperation Foundation

(*) Notice: Subject to any disclaimer, the term of this patent is extended or adjusted under 35 U.S.C. 154(b) by 509 days.

(21) Appl. No.: 11/879,999

(22) Filed: Jul. 19, 2007

(65) Prior Publication Data

US 2008/0300503 A1 Dec. 4, 2008

(30) Foreign Application Priority Data

Jun. 4, 2007 (KR) .................. 10-2007-0054379

(51) Int. Cl.
*A61B 5/08* (2006.01)
(52) U.S. Cl. .................. 600/534; 600/538; 600/529
(58) Field of Classification Search ......... 600/529–543, 600/484
See application file for complete search history.

(56) References Cited

U.S. PATENT DOCUMENTS

| | | | | |
|---|---|---|---|---|
| 4,308,872 A * | 1/1982 | Watson et al. | ......... | 600/538 |
| 4,391,279 A * | 7/1983 | Stein | ......... | 600/387 |
| 4,815,473 A * | 3/1989 | Watson et al. | ......... | 600/534 |
| 5,913,830 A * | 6/1999 | Miles | ......... | 600/535 |
| 6,287,264 B1 * | 9/2001 | Hoffman | ......... | 600/538 |
| 6,416,471 B1 * | 7/2002 | Kumar et al. | ......... | 600/300 |
| 6,454,708 B1 * | 9/2002 | Ferguson et al. | ......... | 600/300 |
| 6,551,252 B2 * | 4/2003 | Sackner et al. | ......... | 600/536 |
| 6,778,090 B2 * | 8/2004 | Newham | ......... | 340/573.1 |
| 7,094,206 B2 * | 8/2006 | Hoffman | ......... | 600/529 |
| 7,314,451 B2 * | 1/2008 | Halperin et al. | ......... | 600/534 |
| 7,429,247 B2 * | 9/2008 | Okada et al. | ......... | 600/534 |
| 2002/0032386 A1 * | 3/2002 | Sackner et al. | ......... | 600/536 |
| 2002/0120207 A1 * | 8/2002 | Hoffman | ......... | 600/538 |
| 2003/0100843 A1 * | 5/2003 | Hoffman | ......... | 600/538 |
| 2003/0135127 A1 * | 7/2003 | Sackner et al. | ......... | 600/536 |
| 2006/0241510 A1 * | 10/2006 | Halperin et al. | ......... | 600/534 |
| 2006/0282001 A1 * | 12/2006 | Noel et al. | ......... | 600/535 |
| 2007/0293781 A1 * | 12/2007 | Sims et al. | ......... | 600/534 |
| 2008/0077020 A1 * | 3/2008 | Young et al. | ......... | 600/484 |
| 2008/0097250 A1 * | 4/2008 | Tochigi et al. | ......... | 600/595 |
| 2008/0269625 A1 * | 10/2008 | Halperin et al. | ......... | 600/508 |

* cited by examiner

*Primary Examiner*—Charles A Marmor, II
*Assistant Examiner*—Navin Natnithithadha
(74) *Attorney, Agent, or Firm*—Greer, Burns & Crain, Ltd.

(57) ABSTRACT

A method and system is provided for monitoring a respiratory signal by radio. The method includes the steps of: converting a change in electric resistance, which is caused by a change in abdominal circumference measured through a rubber waistband that is made of conductive rubber and is mounted on a lower garment of a testee during respiration, into a voltage signal, performing A/D conversion on the voltage signal, and transmitting the converted digital signal to a short distance by radio using a wireless communication protocol for ZigBee; and receiving the respiratory signal transmitted by radio, transmitting it to a computer unit by wire through an RS-232 port that is a serial communication port, and enabling a tester to monitor the respiratory signal through a screen.

5 Claims, 6 Drawing Sheets

METHOD AND SYSTEM OF MONITORING RESPIRATORY SIGNAL BY RADIO

BACKGROUND OF THE INVENTION

1. Field of the Invention

The present invention relates generally to a method and system of monitoring a biological signal by radio. More particularly, the present invention relates to a method and system of monitoring a respiratory signal by radio, in which a respiratory frequency and a lung volume are precisely measured using an elastic device fastened around the abdomen without the trouble of measuring the biological signal, the respiratory signal, which is most frequently measured for inpatients, through an oral cavity.

2. Description of the Prior Art

In general, respiration is a physiological function that supplies fresh air (oxygen) into the body and then releases a byproduct, carbon dioxide, of the metabolism out of the body, and thus is essential for life. The respiration, blood pressure, pulse, and body temperature are important biological signals showing a vital sign, and thus are the highest measurement frequency of biological signals that must be measured three or four times for all the inpatients of the hospital from day to day. For this reason, whether or not the respiration occurs or measuring and monitoring an amount of respiration is very important medically.

Up to now, respiratory airflow transducer, respiratory inductive plethysmography, contactless respiration measurement, and breathing air temperature measurement have been used or studied for sensing, measuring, and monitoring of a breathing signal.

Figure 1A:
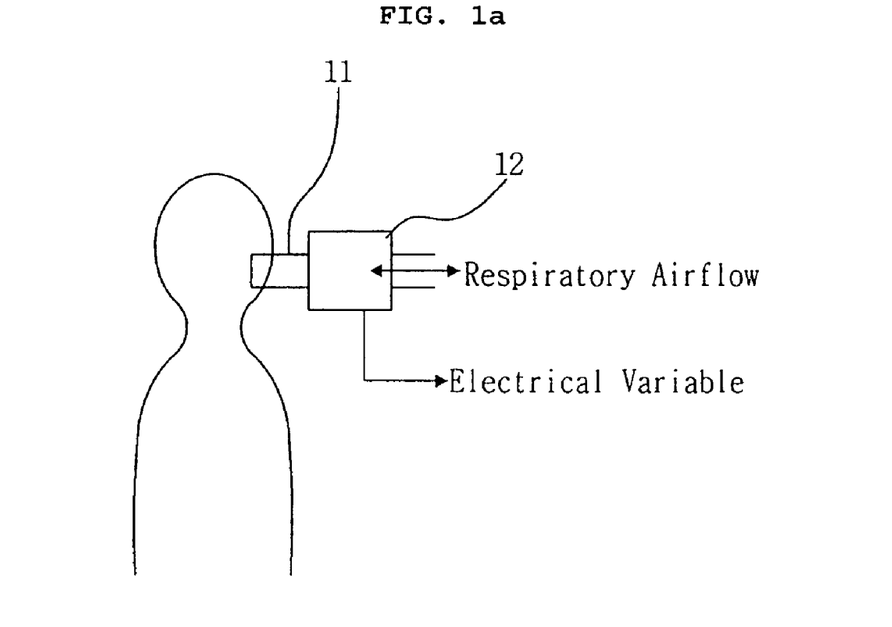
FIG. 1a is a conceptual view for explaining a respiratory airflow transducer used for detecting, measuring, and monitoring a respiratory signal.

As illustrated in FIG. 1a, the respiratory airflow transducer converts an amount of air, which is inhaled when a testee closes the nose to breathe through the mouth with a breathing pipe 11 held in the mouth, into an electrical variable through a flow sensor 12 connected with the breathing pipe 11, and measures an amount of respiration using the electrical variable converted by the flow sensor 12. However, the respiratory airflow transducer is troublesome because the testee must breathe with the breathing pipe 11 held in the mouth. As such, the respiratory airflow transducer is used for a clinical spirometry test that must continuously measure respiratory airflow with precision.

Figure 1B:
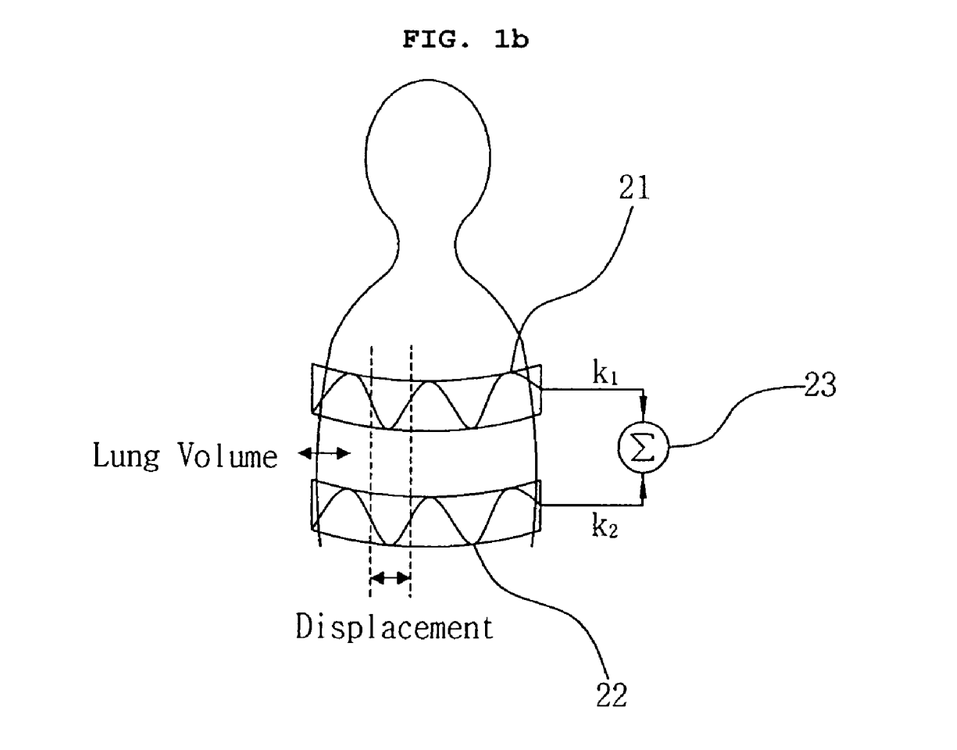
FIG. 1b is a conceptual view for explaining a respiratory inductive plethysmogrpahy used for detecting, measuring, and monitoring a respiratory signal.

As illustrated in FIG. 1b, the respiratory inductive plethysmography is a technique of measuring a change of the skin without the trouble of holding the breathing pipe in the mouth of a testee, thereby estimating a lung volume. In other words, the lung volume is estimated by contraction and expansion of the lung. More specifically, the lung volume is estimated by measuring and summing up changes of the peripheries of the thorax and abdomen caused by the respiration on the basis of a principle that the respiration causes the volumes of the thorax and abdomen to be changed.

Elastic bands, in which thorax and abdomen coils 21 and 22 of conductive metal are disposed in a zigzag shape, are fastened to the thorax and abdomen of the testee, respectively. As the peripheries of the thorax and abdomen of the testee, to whom the thorax coil 21 and the abdomen coil 22 are attached breathes, are varied while the testee breathes, a distance between the adjacent crests (or roots) of each zigzag coil is varied or displaced. Thereby, the inductances 23 of the thorax and abdomen coils that are attached to the thorax and the abdomen are changed and measured electrically. At this time, although the lung volumes are equal to each other, the contributions of the thorax and the abdomen to the lung volumes are dependent on the testee. Thus, the relative contributions $k_1$ and $k_2$ of each testee are calculated and applied in advance.

However, the respiratory inductive plethysmography is difficult to handle, and furthermore is impossible to wash with water, because the separate elastic bands must be fastened on the clothes and because the metal coils are attached in the elastic bands. Further, because the AC signal is required to measure the change of the inductance, a signal extracting circuit, which includes circuits of generating and measuring the AC signal having constant frequency and amplitude, becomes complicated.

Figure 1C:
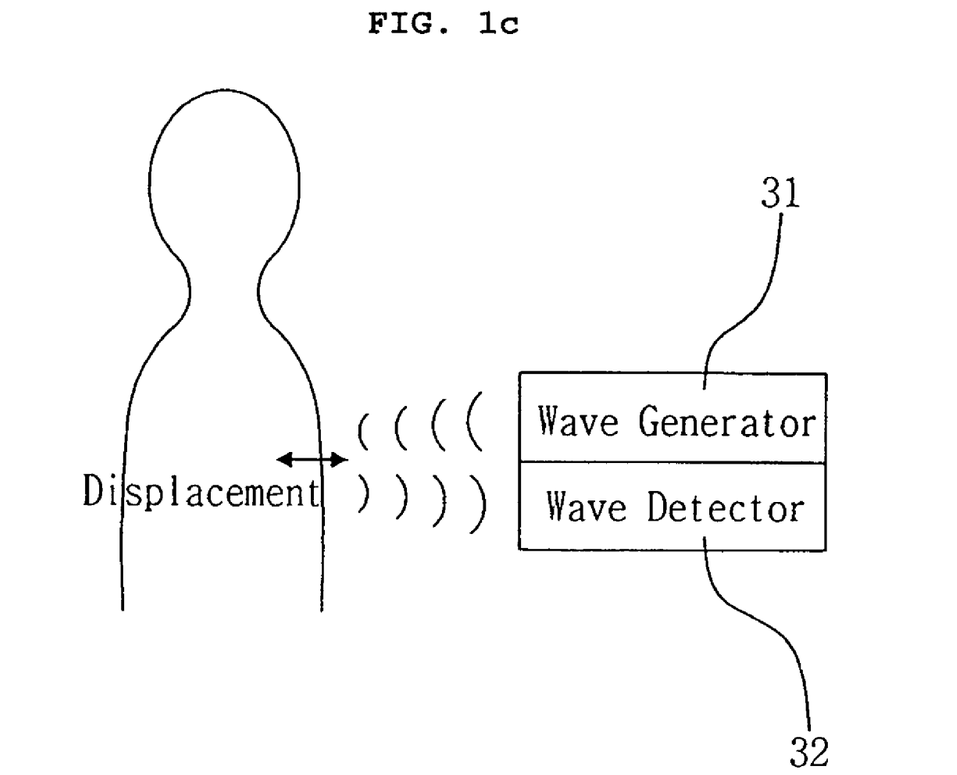
FIG. 1c is a conceptual view for explaining contactless respiration measurement used for detecting, measuring, and monitoring a respiratory signal.

As illustrated in FIG. 1c, the contactless respiration measurement is a technique for detecting respiration with no contact between a device and the body, and makes use of the fact that during respiration, the skin of the thorax moves backwards and forwards to undergo displacement. More specifically, a wave generator 31 generates waves such as ultrasonic waves or electromagnetic waves, and then sends the waves to the front of the body. Thus, the waves are reflected from the body. At this time, a wave detector 32 detects properties of the reflected waves, and compares the reflected waves with the incident waves. Thereby, the displacement caused by the periodic motion of the physical skin is measured. However, the wave signals are greatly attenuated in the air, and thus become weak. As a result, a quality of measurement becomes very bad. Furthermore, if the waves are not accurately emitted to the front of the body in the direction perpendicular to the front of the body, such measurement is impossible. The wave generator and detector are difficult to produce in the technical aspect, and thus have high production cost. Due to this problem, the contactless respiration measurement is under the development, and thus has a small possibility of practical use.

Figure 1D:
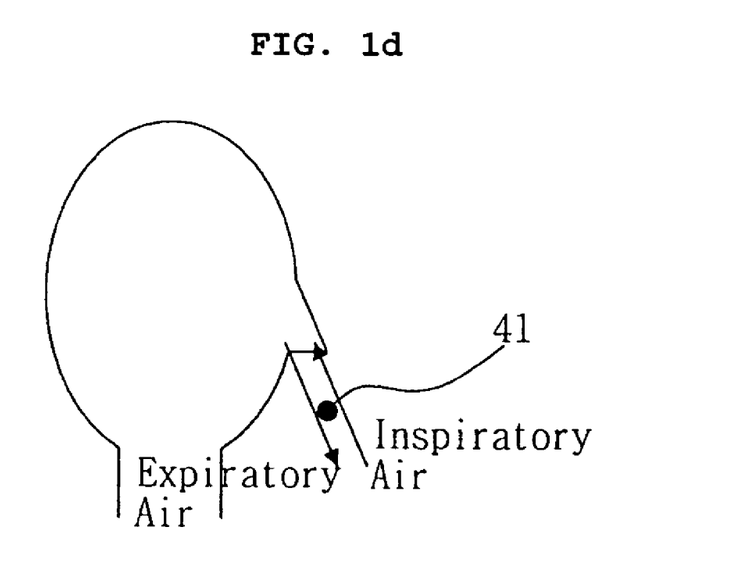
FIG. 1d is a conceptual view for explaining breathing air temperature measurement used for detecting, measuring, and monitoring a respiratory signal.

As illustrated in FIG. 1d, the breathing air temperature measurement is a technique based on the facts that, because a room temperature and a body temperature are is about 25° C. and about 37° C. respectively, a difference between the room temperature and the body temperature is about 10° C., and that, because a temperature of expiratory air when a testee exhales is equal to the body temperature, it is higher than that of inspiratory air when the testee inhales.

When a sensor (e.g. thermocouple or thermistor) 41 for sensing a temperature is located near the nostrils of the testee, a period of temperature change is equal to a respiratory period, so that it can be calculated to measure a respiratory frequency. However, this technique can measure only the respiratory frequency, but not a variable related to ventilation (i.e. the volume of air breathed in and out of the lungs) such as a lung volume. According to the normal physiological function of the body, the lung volume is increased first when the metabolism of the body increases to require increasing the ventilation, and then the respiratory frequency is increased only for still greater ventilation. Taking this fact into consideration, the measurement of the respiratory frequency makes it possible to determine whether or not the respiration occurs, but it makes it impossible to measure the ventilation that is more important than the respiratory frequency from the physiological viewpoint.

SUMMARY OF THE INVENTION

Accordingly, the present invention has been made keeping in mind the above problems occurring in the prior art, and a first object of the present invention is to provide a method of monitoring a respiratory signal by radio, in which the respiratory signal is monitored using an elastic waistband made of conductive rubber is fastened around the abdomen of a testee without the trouble of holding the breathing pipe in the mouth of the testee, thereby providing a personal customized respiratory measurement technique that accurately measures a respiratory frequency and measures a lung volume within an allowable error range, and transmitting and monitoring the measured respiratory signal by radio.

A second object of the present invention is to provide a system for accomplishing the first object.

To accomplish these objects, according to one aspect of the present invention, there is provided a method of monitoring a respiratory signal by radio. The method comprises: a respiratory signal measuring and transmitting step of converting a change in electric resistance, which is caused by a change in abdominal circumference measured through a rubber waistband that is made of conductive rubber and is mounted on a lower garment of a testee during respiration, into a voltage signal, performing analog/digital (A/D) conversion on the voltage signal, and transmitting the converted digital signal to a short distance by radio using a wireless communication protocol for ZigBee; and a respiratory signal receiving and monitoring step of receiving the respiratory signal transmitted by radio, transmitting it to a computer unit by wire through an RS-232 port that is a serial communication port, and enabling a tester to monitor the respiratory signal through a screen.

According to another aspect of the present invention, there is provided a system of monitoring a respiratory signal by radio. The system comprises: a connector that is connected to opposite ends of a rubber waistband, the rubber waistband being mounted on a lower garment of a testee and being made of rubber including conductive particles; a radio transmitter that is electrically connected with the connector, converts a change in electric resistance, which is caused by a change in abdominal circumference measured through the rubber waistband during respiration, into a voltage signal, performs analog/digital (A/D) conversion on the voltage signal, and transmits the converted digital signal to a short distance by radio using a wireless communication protocol for ZigBee; and a radio receiver that receives the respiratory signal, transmitted by radio using the ZigBee wireless communication protocol, through a reception antenna, converts the respiratory signal into serial information, and outputs the converted serial information through a RS-232 port. The respiratory signal is monitored by calculating the input respiratory signal and checkup parameters at the radio receiver, and outputting the calculated result to a monitor screen.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, exemplary embodiments of the present invention will be described in detail.

Figure 2:
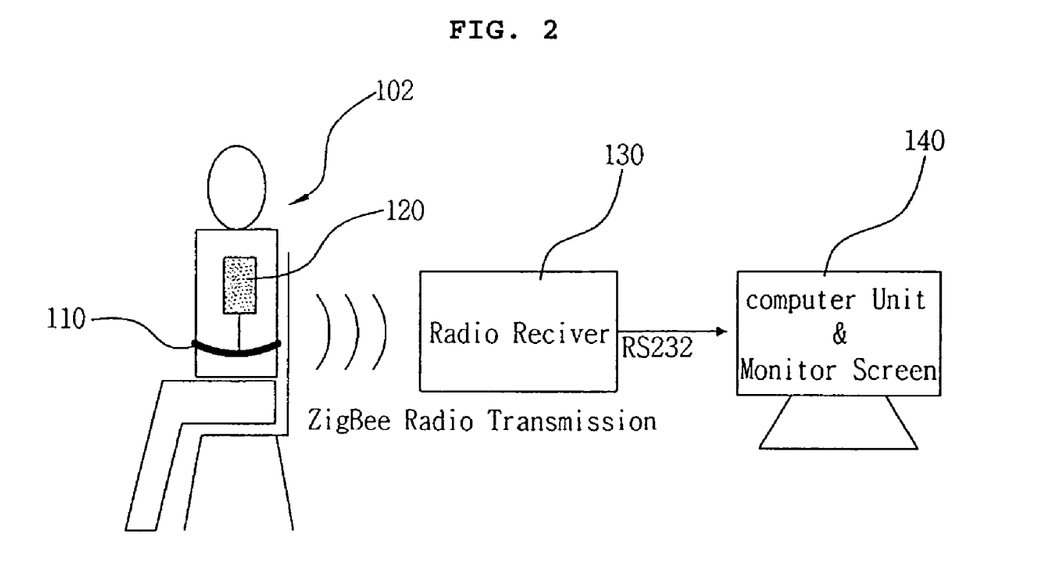
FIG. 2 is a conceptual view for explaining configuration and operation of a system of monitoring a respiratory signal by radio according to the present invention.
Figure 3:
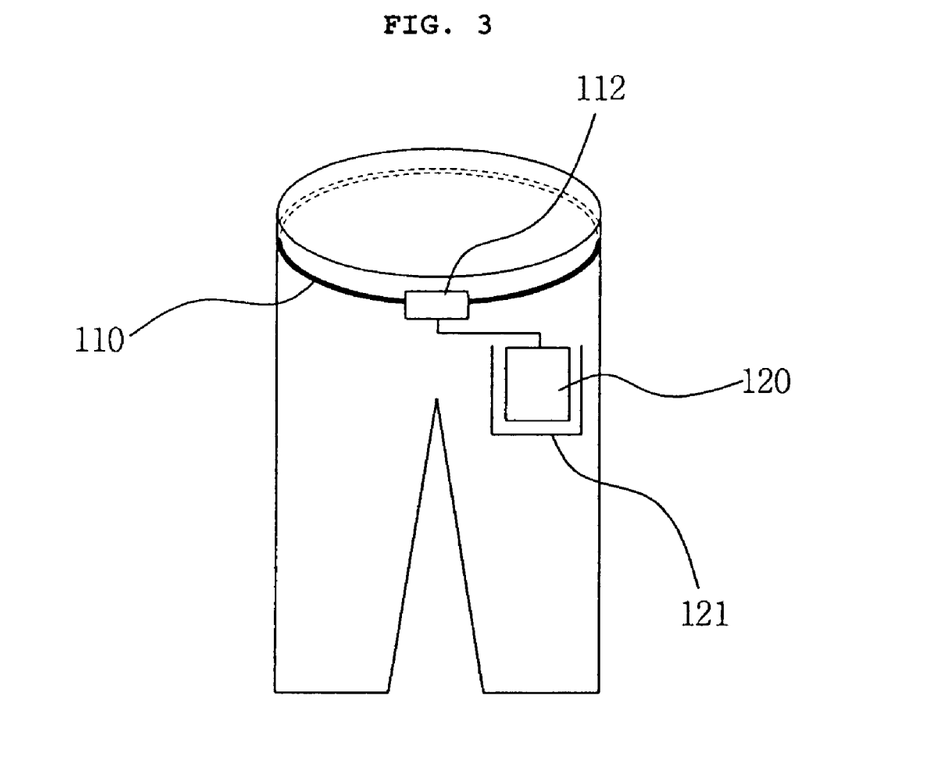
FIG. 3 is a view illustrating an embodiment in which a rubber waistband for the system of FIG. 2 is mounted on a lower garment worn by a testee

FIG. 2 is a conceptual view for explaining configuration and operation of a system of monitoring a respiratory signal by radio according to the present invention. FIG. 3 is a view illustrating an embodiment in which a rubber waistband for the system of FIG. 2 is mounted on a lower garment worn by a testee.

As illustrated in FIG. 2, the system of monitoring a respiratory signal by radio according to the present invention includes a rubber waistband 110, which is mounted in a lower garment worn by a testee 102. The rubber waistband 110 mounted on the trousers is made of conductive rubber having electrical conductivity, rather than ordinary rubber having electrical non-conductivity. Owing to the elasticity, the rubber waistband 110 also functions as a belt for the waist.

While the testee respires, the abdomen of the testee is changed in circumference, and simultaneously the rubber waistband 110 elongates (i.e., expands) or contracts. The rubber waistband 110 therefore changes in cross section and length, and thereby changes in electric resistance. A radio transmitter 120 connected to the rubber waistband 110 converts the electric resistance change, which is input through the rubber waistband 110, into an analog voltage signal, performs A/D conversion on the voltage signal, and transmits the respiratory signal based on digital information to a short distance using a wireless communication protocol for ZigBee.

The radio transmitter 120 is put into a pocket of the lower or upper garment of the testee in electrical connection with the rubber waistband 110. The ZigBee wireless communication protocol applied to the radio transmitter 120 conforms to the IEEE 802.15.4 wireless standard for data networks, operates in frequency bands 2.4 GHz, 868 MHz, and 915 MHz, uses direct-sequence spread spectrum (DSSS) coding, has a data transfer rate from 20 kbps to 250 kbps.

The radio signal transmitted from the radio transmitter 120 is received by a radio receiver 130. The radio receiver 130 receives the respiratory signal transmitted using the ZigBee wireless communication protocol, and transmits it to a computer unit 140 such as a personal computer (PC) by wire through an RS-232 port that is a serial communication port, so that it enables a tester to monitor the respiratory signal through a screen.

The respiratory signal transmitted to the computer unit 140 is continuously displayed on the screen, and exhibits clinically important checkup parameters, such as a tidal volume, a respiration frequency, and a minute ventilation, at fixed periods.

The testee is guaranteed mobility within a predetermined distance in which transmission and reception are performed by radio, and the respiratory signal of the testee is transmitted and monitored by radio without a stop in motion. Accordingly, the trouble of the testee is reduced during the respiration checkup.

As illustrated in FIG. 3, among the components of the present invention, the rubber waistband used to sense the abdominal circumference change is made of conductive rubber, is mounted on the lower garment, which is typically worn by an inpatient, and also serves as the belt for the waist. In the present invention, the opposite ends of the rubber waistband 110 are connected to a connector 112 that can be connected using an electric wire. The connector 112 is electrically connected with the radio transmitter 120, which is adapted to be carried in the pocket 121 of the lower or upper garment of the testee. Thus, the rubber waistband of the lower garment of the testee functions as a respiratory sensor by itself without mounting a separate sensor unit for measuring the respiratory signal.

The conductive rubber used for the rubber waistband 110 of the present invention is produced by mixing a small quantity of conductive particles (e.g. of carbon, platinum, etc.) when a rubber as a nonconductor is formed in a desired shape. In this case in which the conductive rubber is produced so as to have the range from tens of $\Omega$ to several k$\Omega$ according to a mixing ratio, the electric resistance change caused by the change in length can be easily measured.

Figure 4:
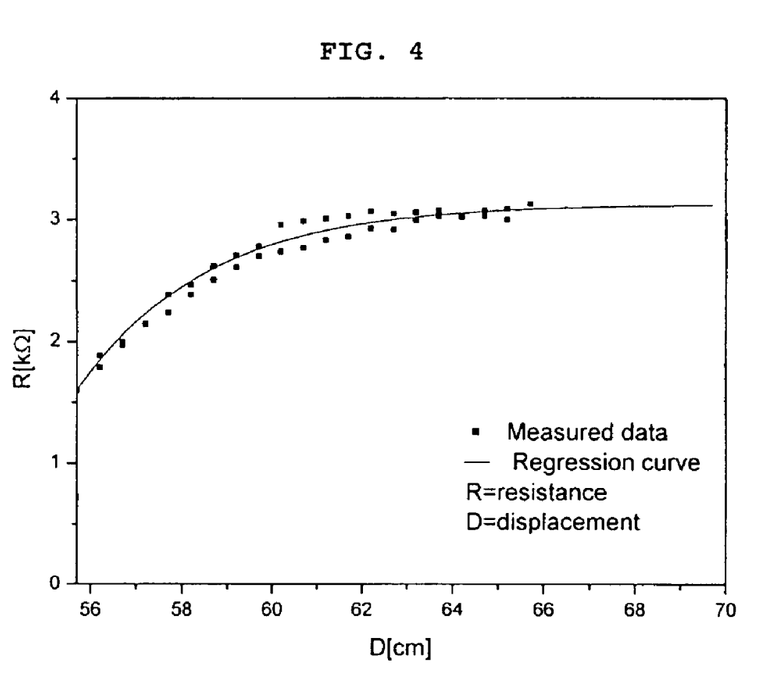
FIG. 4 is a graph illustrating a change in electric resistance measured while elongating the rubber waistband of FIGS. 2 and 3 by 0.5 cm.
Figure 5:
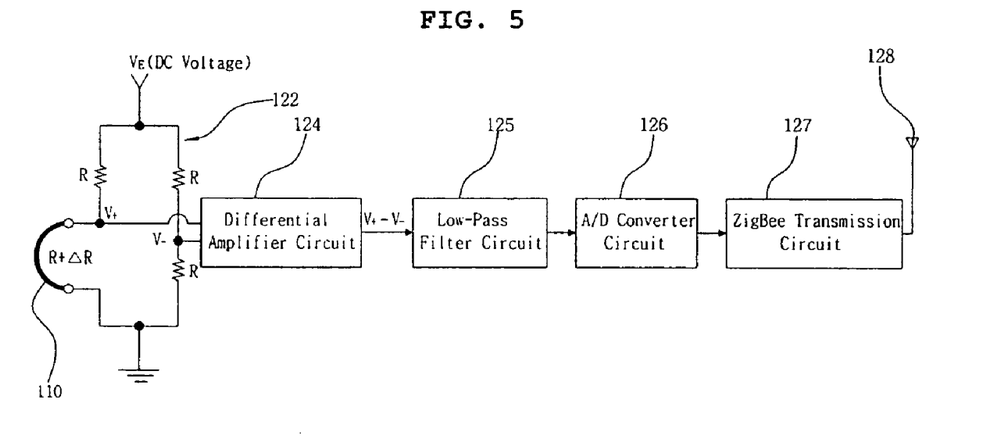
FIG. 5 is a block diagram for explaining the configuration and operation of a radio transmitter in a system of monitoring a respiratory signal by radio according to the present invention.
Figure 6:
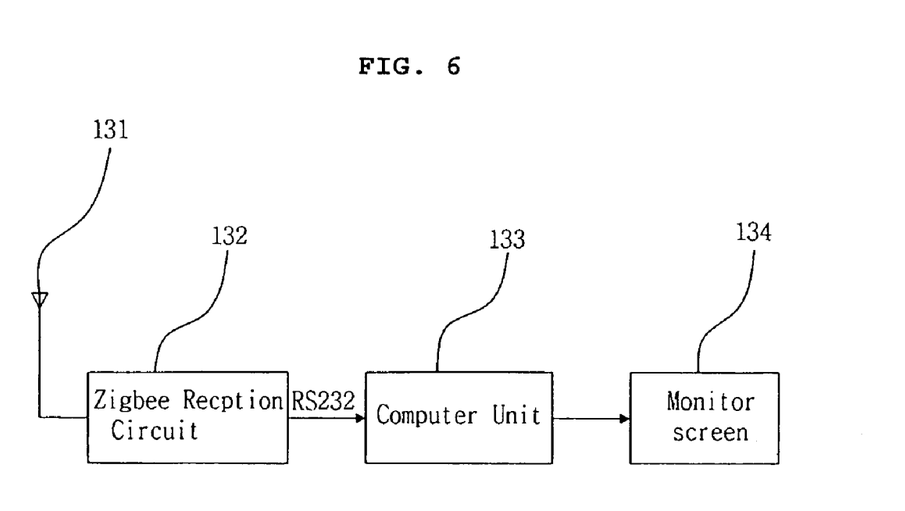
FIG. 6 is a block diagram for explaining the configuration and operation of a radio receiver in a system of monitoring a respiratory signal by radio according to the present invention.

FIG. 4 is a graph illustrating a change in electric resistance measured whenever the rubber waistband of FIGS. 2 and 3. is elongated by 0.5 cm. FIG. 5 is a block diagram for explaining the configuration and operation of a radio transmitter in a system of monitoring a respiratory signal by radio according to the present invention. Further, FIG. 6 is a block diagram for explaining the configuration and operation of a radio receiver in a system of monitoring a respiratory signal by radio according to the present invention.

As illustrated in FIG. 4, the rubber waistband 110 of the present invention is cut to a proper length so as to be mounted on the lower garment, and then the change of electric resistance is measured whenever the cut rubber waistband 110 is gradually elongated by 0.5 cm. As a result, as the length of the rubber waistband 110 increases, a value of the electric resistance is increased exponentially.

In this manner, when the length is changed within a range of 1 cm or less (range from 56 cm to 57 cm in FIG. 4), the electric resistance shows linear correlation in which it is almost proportional to the length. When the respiratory signal is measured within this range, an optimal sensitivity of measurement can be obtained. In other words, while the abdominal circumference of the testee is periodically changed by the respiration of the testee, the electric resistance of the rubber waistband 110 mounted on the lower garment of the testee is alternately increased and decreased.

The electric resistance change measured through the rubber waistband 110 is input into the radio transmitter 120. As illustrated in FIG. 5, the radio transmitter 120 establishes a circuit such that the electric resistance of the rubber waistband 110 operates to have the resistance in one arm (of four arms) of the Wheatstone bridge circuit 122. It is assumed that the electric resistance of the expanded rubber waistband 110 when the testee exhales is R. The rubber waistband 110 is connected with three resistors having the same resistance as the electric resistance thereof, and thereby the bridge circuit is constructed. At this time, voltages $V_+$ and $V_-$ on the bridge circuit are expressed by the following Equation 1.

$$V_+ = V_- = \frac{V_E}{2} \qquad (1)$$

In Equation 1, $V_E$ is the DC voltage that drives the bridge circuit.

When the testee begins to inhale, the electric resistance increases to R+$\Delta$R, and thus the voltage V+ of Equation 1 is transformed into the following Equation 2.

$$V_+ = \frac{R+\Delta R}{R+(R+\Delta R)} V_E = \frac{1+\frac{\Delta R}{R}}{1+1+\frac{\Delta R}{R}} V_E \qquad (2)$$

In Equation 2, if the change $\Delta$R of the electric resistance that is increased by inhalation is sufficiently less than R (i.e. R>>$\Delta$R), $\Delta$R/R of the denominator is approximated to 0, and thus Equation 2 is transformed into the following Equation 3.

$$V_+ \approx \frac{1+\frac{\Delta R}{R}}{2} V_E = \frac{V_E}{2} + \frac{\Delta R}{2R} V_E \qquad (3)$$

In Equation 3, because the voltage $V_-$ maintains the value, $V_E/2$, of Equation 1 irrespective of the elongation of the conductive rubber waistband (FIG. 5), a difference between $V_+$ and $V_-$ is calculated, and thereby is expressed by the following Equation 4.

$$V_+ - V_- = \frac{\Delta R}{2R} V_E \qquad (4)$$

Accordingly, the voltage difference between $V_+$ and $V_-$ is proportional to the electric resistance change $\Delta$R of the conductive rubber waistband. In other words, when the DC Wheatstone bridge circuit 122 of FIG. 5 is used, the electric resistance change is converted into a voltage signal. The voltage signal output from the Wheatstone bridge circuit 122 is applied to a differential amplifier circuit 124, and then the differential amplifier circuit 124 amplifies and outputs a difference between the input $V_+$ and $V_-$voltage signals to one voltage signal.

The voltage signal amplified by the differential amplifier circuit 124 is applied to a low-pass filter circuit 125, and then the low-pass filter circuit 125 extracts a voltage signal corresponding to the respiratory signal, from which high-band noise is minimized by allowing only a low-band signal to pass therethrough.

The respiratory signal output from the low-pass filter circuit 125 is input into an A/D converter circuit 126, and thereby is converted into a digital signal. In other words, because the respiratory signal output from the low-pass filter circuit 125 is an analog voltage signal, it is converted into a digital signal (information) by the A/D converter circuit 126.

The digital signal output from the A/D converter circuit 126 is input into a ZigBee transmission circuit 127, and then is transmitted to a short distance through a transmission antenna 128 by radio. The A/D converter circuit and the ZigBee transmission circuit can be easily realized using a commercialized semiconductor chip. Since the entire radio transmitter 120 can be configured of a low electric power circuit, it can be operated with a dry battery, and be reduced in size when produced. As a result, the radio transmitter is designed to be carried in a pocket of a lower or upper garment of the testee. In this manner, because the radio transmitter 120 is carried in the pocket, the respiratory signal of the testee can be freely monitored during moving within a range in which it can be received by radio.

As illustrated in FIG. 6, the respiratory signal, which is transmitted from the ZigBee transmission circuit 127 of the radio transmitter by radio, is input into a ZigBee reception circuit 132 of the radio receiver 130 through a reception antenna 131, is converted into serial information, and is input into the computer unit 133 through the RS-232 port. The computer unit 133 functions to display the respiratory signal and the whole checkup parameters on the monitor screen 134, and to perform respiratory monitoring for which a user makes a request.

Figure 7:
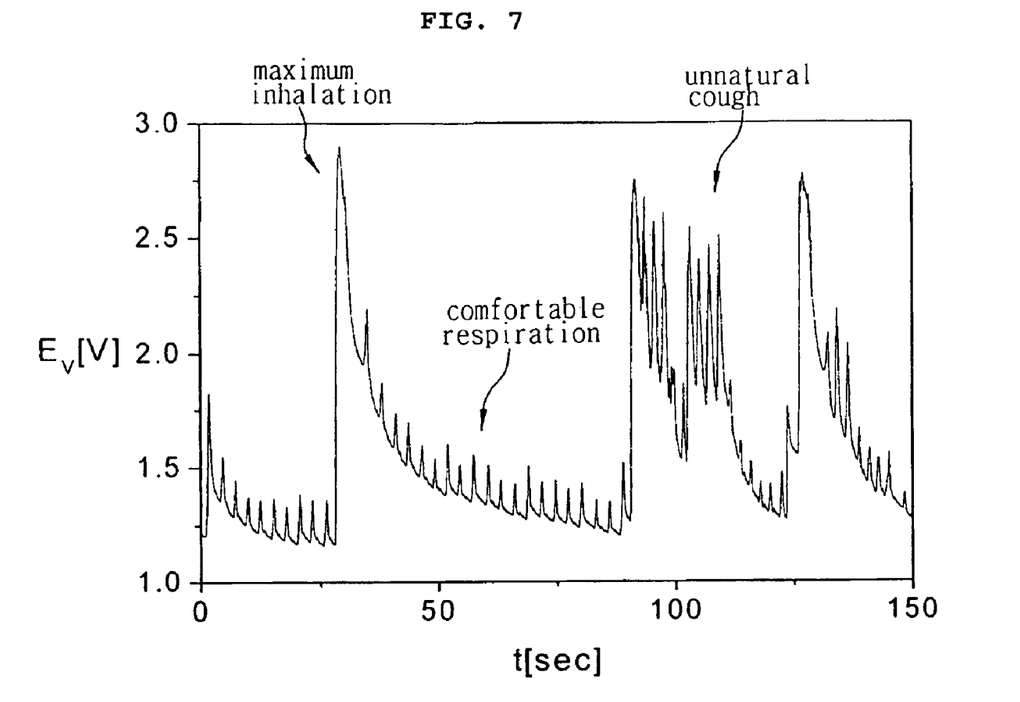
FIG. 7 is a graph showing the result of a respiratory monitoring (change in output voltage based on respiration) test using a system of monitoring a respiratory signal by radio according to the present invention.
Figure 8:
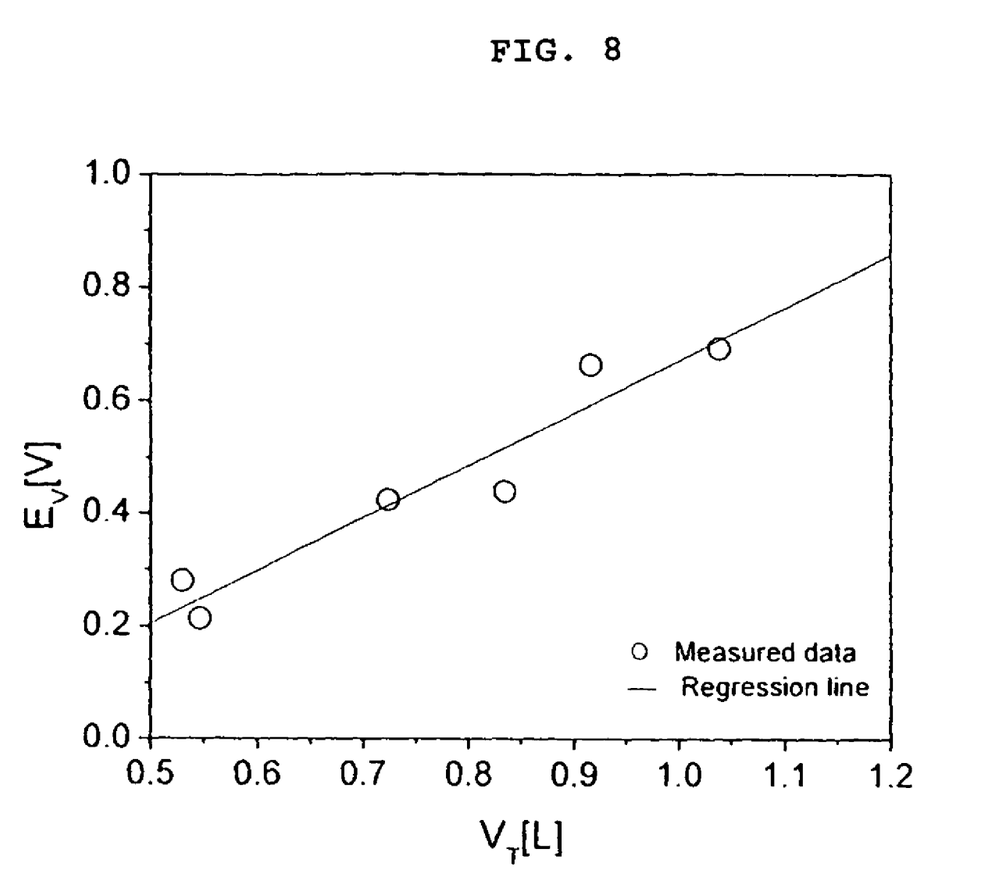
FIG. 8 is a graph showing correlation between abdominal respiratory signal and tidal volume of a particular testee in a $CO_2$ inhalation test performed for respiratory monitoring in a patient personal customized type using a system of monitoring a respiratory signal by radio according to the present invention.

FIG. 7 is a graph showing the result of a respiratory monitoring test (change of output voltage based on respiration) using a system of monitoring a respiratory signal by radio according to the present invention. FIG. 8 is a graph showing correlation between abdominal respiratory signal and tidal volume of a particular testee in a $CO_2$ inhalation test performed for respiratory monitoring in a patient personal customized type using a system of monitoring a respiratory signal by radio according to the present invention.

FIG. 7 shows the test result using the system of monitoring a respiratory signal by radio according to the present invention. The testee sequentially performed comfortable respiration, maximum inhalation, comfortable respiration, unnatural cough, and maximum inhalation in the state where he/she sited on a chair in the lower garment on which the conductive rubber waistband was mounted. At that time, the respiratory signals were monitored by radio.

In FIG. 7, the vertical axis represents the time, and the horizontal axis represents the voltage. It can be found that accurate respiratory frequencies were obtained because respective respiratory modes (patterns) were easily discriminated by obtained respiratory signals, and because periodical respiration was accurately recognized. Because the possibilities of measuring the accurate respiratory frequencies and simultaneously discriminating the respiratory modes were proved as shown in FIG. 7, a measurement test of the lung volume, as shown in FIG. 8, was performed in a manner such that, in order to increase a tidal volume without being unconscious of his/her respiration in a normal state, the testee breathed a mixed gas consisting of carbon dioxide from 0% to 5% and air through the mouth for three minutes, and the respiratory signals were monitored for one minute when reaching a steady state The testee held a respiratory airflow transducer in his/her mouth, and then accurate respiratory airflow and a tidal volume were measured together with an abdominal respiratory signal. It can be seen from the correlation between the abdominal respiratory signal and the tidal volume as shown in FIG. 8 that the abdominal respiratory signal increased when the tidal volume increased by $CO_2$ inhalation, and was statistically significant ($P<0.005$) because a coefficient of correlation was over 0.96.

Therefore, the fact that the system of monitoring a respiratory signal by radio according to the present invention could estimate the tidal volume in a relatively accurate manner by monitoring the respiratory signal from the conductive rubber waistband 110 by radio was experimentally proved.

As described above, when the abdominal respiratory signals are monitored using the conductive rubber waistband (or belt), the respiratory frequencies can be accurately measured without an error as in the graph of FIG. 7, and the tidal volume has linear correlation with respect to an actual true value within a relative error from 10% to 20%.

This relative error is attributed to a relative ratio at which the respiration varies the volumes of the thorax and abdomen and is distributed to the thorax and the abdomen. As such, the contribution of the thorax is regarded as nothing in the present invention because only the tidal volume of the abdomen is measured. Although the contributions of the thorax and abdomen are different from each other depending on the testees, they are invariably maintained to each particular testee. Thus, the tidal volume can be reliably measured even when it is measured respect to only the abdomen. In other words, after each testee is subjected to customized calibration in terms of an individual difference, the respiratory signals are measured. Thereby, accurate measurement results can be obtained.

The system of monitoring a respiratory signal by radio according to the present invention is designed so that the elastic conductive rubber waistband (or belt) serving as the respiratory sensor is mounted on the lower garment of the patient. The lower garments are not exchanged between the patients, so that the personal customized calibration is effective. As shown in FIG. 8, in order to carry out the personal customized calibration, a calibration procedure of performing the $CO_2$ inhalation test on each testee once, obtaining the correlation between the abdominal respiratory signal and the tidal volume of the particular testee, calculating a regression line, which obtains the lung volume from the abdominal respiratory signal, from the correlation, and then substituting the abdominal respiratory signal into the regression line to measure the lung volume has only to be performed in advance.

As can be seen from the foregoing, the present invention improves convenience of use because it does not provide the trouble of mounting a separate unit in the mouth or nose when the respiratory signals is measured and checked up, can be cleaned due to the conductive rubber material unlike a complete conductor, and can be the garment wearable type serving as the belt for the waist. Further, because the DC is used instead of the AC when the signal is extracted, the circuit is simplified. Due to the radio transmission mode, the measurement is performed in a free state without restricting activity of the patient. Furthermore, the respiratory monitoring is possible during moving. In addition, the accurate lung volume can be estimated only by the abdomen respiratory measurement through the personal customized calibration.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method of monitoring a respiratory signal by radio, the method comprising:

attaching a single rubber waistband that is made of a conductive rubber to a lower garment of a testee so that the waistband completely surrounds the testee's body;

a respiratory signal measuring and transmitting step of converting a change in electric resistance, which is caused by a change in abdominal circumference measured through the rubber waistband during respiration, into a voltage signal, performing analog/digital (A/D) conversion on the voltage signal, and transmitting the converted digital signal to a short distance by radio using a wireless communication protocol for ZigBee; and a respiratory signal receiving and monitoring step of receiving the respiratory signal transmitted by radio, transmitting it to a computer unit by wire through an RS-232 port that is a serial communication port, and enabling a tester to monitor the respiratory signal through a screen.

2. The method as claimed in claim 1, wherein the rubber waistband is produced by mixing conductive particles into rubber so as to have the electric resistance from tens of $\Omega$ to several k$\Omega$.

3. The method as claimed in claim 1, wherein the rubber waistband in the respiratory signal measuring and transmitting step is operated by one of four resistors constituting a Wheatstone bridge circuit, and undergoes the conversion of the electric resistance change thereof into the voltage signal.

4. The method as claimed in claim 1, wherein the voltage signal converted by the electric resistance change of the rubber waistband corresponds to the respiratory signal that is amplified through a differential amplifier circuit and minimizes high-band noise through a low pass filter circuit.

5. The method as claimed in claim 1, wherein, prior to the respiratory signal receiving and monitoring step, a calibration procedure of performing a $CO_2$ inhalation test on each testee once, analyzing correlation between an abdominal respiratory signal and a tidal volume of the testee to calculate a regression line, and substituting the abdominal respiratory signal, measured in the respiratory signal measuring and transmitting step, into the regression line to measure the lung volume.

* * * * *